(12) United States Patent
Libbus et al.

(10) Patent No.: US 7,881,782 B2
(45) Date of Patent: Feb. 1, 2011

(54) NEURAL STIMULATION SYSTEM TO PREVENT SIMULTANEOUS ENERGY DISCHARGES

(75) Inventors: Imad Libbus, St. Paul, MN (US); Andrew P. Kramer, Stillwater, MN (US); William J. Linder, Golden Valley, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 813 days.

(21) Appl. No.: 11/110,542

(22) Filed: Apr. 20, 2005

(65) Prior Publication Data

US 2006/0241699 A1    Oct. 26, 2006

(51) Int. Cl.
*A61N 1/18* (2006.01)
(52) U.S. Cl. .......................................................... 607/2
(58) Field of Classification Search ................... 607/2, 607/4, 5, 9, 42
See application file for complete search history.

(56) References Cited

U.S. PATENT DOCUMENTS

| | | | |
|---|---|---|---|
| 4,408,608 A | 10/1983 | Daly et al. | |
| 5,161,527 A * | 11/1992 | Nappholz et al. | 607/14 |
| 5,199,428 A | 4/1993 | Obel et al. | |
| 5,203,326 A * | 4/1993 | Collins | 607/4 |
| 5,292,338 A * | 3/1994 | Bardy | 607/5 |
| 5,318,592 A | 6/1994 | Schaldach | |
| 5,330,507 A * | 7/1994 | Schwartz | 607/14 |
| 5,334,221 A | 8/1994 | Bardy | |
| 5,356,425 A | 10/1994 | Bardy et al. | |
| 5,411,531 A * | 5/1995 | Hill et al. | 607/14 |
| 5,578,061 A * | 11/1996 | Stroetmann et al. | 607/4 |
| 5,792,187 A | 8/1998 | Adams | |
| 5,817,131 A | 10/1998 | Elsberry et al. | |
| 5,916,239 A | 6/1999 | Geddes et al. | |

(Continued)

FOREIGN PATENT DOCUMENTS

EP    0547734 A2    6/1993

(Continued)

OTHER PUBLICATIONS

"International Search Report and Written Opinion for Application No. PCT/US2006/014877, date mailed Sep. 25, 2006", 13 Pages.

(Continued)

*Primary Examiner*—Niketa I Patel
*Assistant Examiner*—Joseph Stoklosa
(74) *Attorney, Agent, or Firm*—Schwegman, Lundberg & Woessner, P.A.

(57) ABSTRACT

Various aspects of the present subject matter relate to a system. Various embodiments of the system comprise at least one port to connect to at least one lead with at least one electrode, at least one stimulator circuit and at least one controller. The at least one stimulator circuit is connected to the at least one port and is adapted to deliver neural stimulation to a neural stimulation target using the at least one electrode. The at least one controller is adapted to determine when another energy discharge other than the neural stimulation to the neural stimulation target is occurring and to prevent delivery of the neural stimulation simultaneously with the other energy discharge. Other aspects and embodiments are provided herein.

43 Claims, 10 Drawing Sheets

U.S. PATENT DOCUMENTS

| | | | |
|---|---|---|---|
| 6,006,134 A | 12/1999 | Hill et al. | |
| 6,073,048 A | 6/2000 | Kieval et al. | |
| 6,134,470 A | 10/2000 | Hartlaub | |
| 6,341,236 B1 | 1/2002 | Osorio et al. | |
| 6,363,278 B1 | 3/2002 | Stahmann et al. | |
| 6,895,273 B2 * | 5/2005 | Seim et al. | 607/14 |
| 7,123,961 B1 | 10/2006 | Kroll et al. | |
| 7,184,828 B2 * | 2/2007 | Hill et al. | 607/2 |
| 7,277,761 B2 | 10/2007 | Shelchuk | |
| 2002/0072776 A1 | 6/2002 | Osorio et al. | |
| 2003/0040774 A1 | 2/2003 | Terry et al. | |
| 2003/0078623 A1 | 4/2003 | Weinberg et al. | |
| 2003/0100925 A1 | 5/2003 | Pape et al. | |
| 2003/0181951 A1 | 9/2003 | Cates | |
| 2003/0229380 A1 | 12/2003 | Adams et al. | |
| 2004/0138721 A1 | 7/2004 | Osorio et al. | |
| 2004/0172074 A1 | 9/2004 | Yoshihito | |
| 2004/0172075 A1 | 9/2004 | Shafer et al. | |
| 2004/0199210 A1 | 10/2004 | Shelchuk | |
| 2004/0215289 A1 | 10/2004 | Fukui | |
| 2004/0254612 A1 | 12/2004 | Ben Ezra et al. | |
| 2005/0143779 A1 | 6/2005 | Libbus | |
| 2005/0143785 A1 | 6/2005 | Libbus | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149156 A1 | 7/2005 | Libbus et al. | |
| 2005/0251216 A1 | 11/2005 | Hill et al. | |
| 2005/0261741 A1 | 11/2005 | Libbus et al. | |
| 2006/0079945 A1 | 4/2006 | Libbus | |
| 2006/0106429 A1 | 5/2006 | Libbus et al. | |
| 2006/0116737 A1 | 6/2006 | Libbus | |
| 2007/0142871 A1 | 6/2007 | Libbus et al. | |

FOREIGN PATENT DOCUMENTS

| | | |
|---|---|---|
| EP | 1426078 A1 | 6/2004 |
| WO | WO-03099377 A1 | 12/2003 |
| WO | WO-2005113066 A1 | 12/2005 |
| WO | WO-2006113871 A1 | 10/2006 |
| WO | WO-2007078410 A1 | 7/2007 |

OTHER PUBLICATIONS

Bilgutay, A. M., "A new concept in the treatment of hypertension utilizing an implantable electronic device: "Baropacer"", *Trans Am Soc Artif Intern Organs.*, 10, (1964), 387-95.

Li, M., "Vagal nerve stimulation markedly improves long-term survival after chronic heart failure in rats", *Circulation*, 109 (1), (Jan. 6, 2004), 120-4.

Libbus, Imad, "Implantable Device for Treating Epilepsy and Cardiac Rhythm Disorders", U.S. Appl. No. 11/312,178, filed Dec. 21, 2005, 39 Pages.

Sigurdsson, Axel, "The role of neurohormonal activation in chronic heart failure and postmyocardial infarction", *American Heart Journal*, 132 (1 Pt 2 Su), (Jul. 1996), 229-234.

Vanoli, Emilio, "Vagal stimulation and prevention of suddenn death in conscious dogs with a healed myocardial infarction", *Circulation Research*, 68(5), (May 1991), 1471-1481.

* cited by examiner

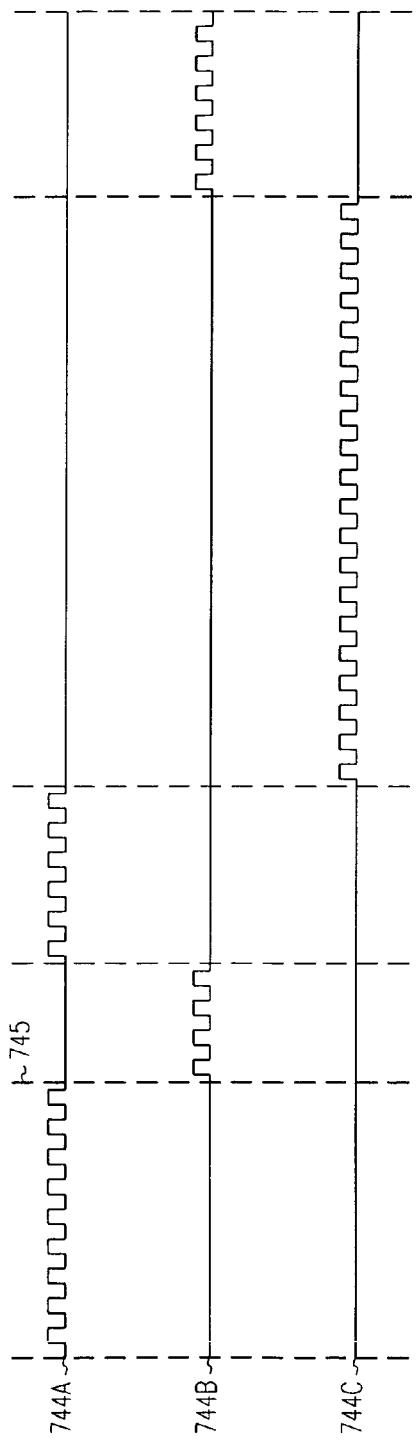
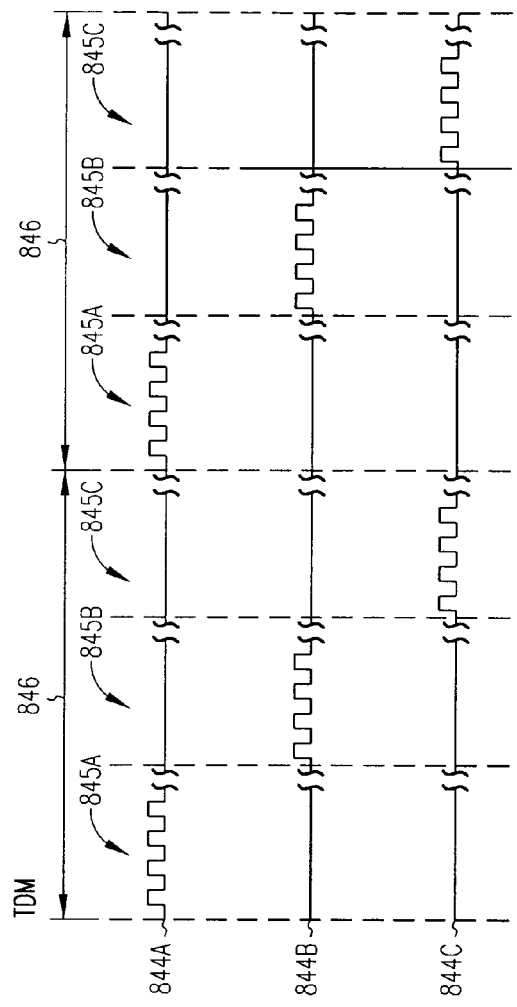

US 7,881,782 B2

NEURAL STIMULATION SYSTEM TO PREVENT SIMULTANEOUS ENERGY DISCHARGES

TECHNICAL FIELD

This application relates generally to medical devices and, more particularly, to neural stimulation systems, devices and methods.

BACKGROUND

Direct electrical stimulation of parasympathetic nerves can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

Different types of therapies can be delivered to treat a condition or to treat different conditions. For example, some neural stimulation therapies involve stimulating two or more neural stimulation targets. Additionally, it possible to deliver both neural stimulation (NS) therapy and cardiac rhythm management (CRM) therapy for some conditions. Some CRM therapies involve stimulating two or more cardiac sites. Some therapies apply pulses to measure an impedance across tissue, and use the impedance measurement to provide a sensed feedback to control the therapies. Thus, therapies can use multiple electrodes to apply current through tissue for the neural stimulation and CRM therapies, and for impedance measurements.

SUMMARY

The present subject matter addresses undesirable interactions that might occur when neural stimulation and another energy discharge occur simultaneously. The neural stimulation has an intended current path through tissue, and the other energy discharge has an intended current path through tissue. However, unintended current paths can occur between electrodes when the neural stimulation and the other energy discharge occur simultaneously. The other energy discharge can be for therapy or diagnostic purposes. Examples of other energy discharges include another neural stimulation to a different neural target or recharge pulses after neural stimulation, a pulse for an impedance measurement such as a minute ventilation pulse, and discharges associated with CRM therapy such as pacing pulses, recharge pulses and defibrillation pulses. The present subject matter prevents neural stimulation from being simultaneously applied when another energy discharge is occurring. Some embodiments stagger the neural stimulation with respect to the other energy discharge(s) to provide at least a few milliseconds between energy discharges, which prevents electrical interactions between pulses without diminishing the effectiveness of the pulses from a physiological perspective.

Various aspects of the present subject matter relate to a system. Various embodiments of the system comprise at least one port to connect to at least one lead with at least one electrode, at least one stimulator circuit and at least one controller. The at least one stimulator circuit is connected to the at least one port and is adapted to deliver neural stimulation to a neural stimulation target using the at least one electrode. The at least one controller is adapted to determine when another energy discharge other than the neural stimulation to the neural stimulation target is occurring and to prevent delivery of the neural stimulation simultaneously with the other energy discharge.

Various aspects of the present subject matter relate to a method. In various embodiments of the method, neural stimulation is delivered to a neural stimulation target, and another energy discharge is provided. It is determined when the other energy discharge is occurring. Delivery of the neural stimulation to the neural stimulation target is prevented when the other energy discharge is occurring.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIG. 7 illustrates neural stimulation to three neural targets whose stimulation is staggered to prevent simultaneous neural stimulation, according to various embodiments of the present subject matter.

FIG. 8 illustrates neural stimulation to three neural targets whose stimulation is staggered using predetermined time slots for a predetermined time period within a time domain multiplexing scheme to prevent simultaneous neural stimulation, according to various embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Implantable medical devices are capable of having independent programmable outputs. If stimulation is delivered simultaneously from capacitive coupled outputs programmed to different pacing voltages, unexpected current pathways are created between outputs. These unexpected currents can add or subtract from the intended current pathway. One problem associated with these unexpected current pathways from simultaneous pacing involves changes in the capture thresholds from the expected capture threshold for the electrodes. Stimulating the outputs one at a time, with a small period of time (e.g. 1 millisecond) separating the end of one stimulation pulse for one output and the beginning of another stimulation pulse for another output, such that the pacing stimulation does not overlap avoids complex intersite current pathways.

The present subject matter addresses undesirable interactions that may occur when neural stimulation is provided simultaneously with another energy discharge, whether for therapy or diagnostic purposes. Examples of another energy discharge include another neural stimulation to a different neural target, a pulse for an impedance measurement such as a minute ventilation pulse, and a discharge associated with a CRM therapy such as a pacing pulse, a recharge pulse and a defibrillation pulse. If the algorithms of the therapy(ies) would simultaneously provide neural stimulation and an energy discharge, the present subject matter overrides the algorithms to stagger the neural stimulation and the other energy discharge. Typically, a few milliseconds is sufficient to prevent electrical interaction. However, a few millisecond discharge typically will not diminish the effectiveness from a physiological perspective.

Figure 1:
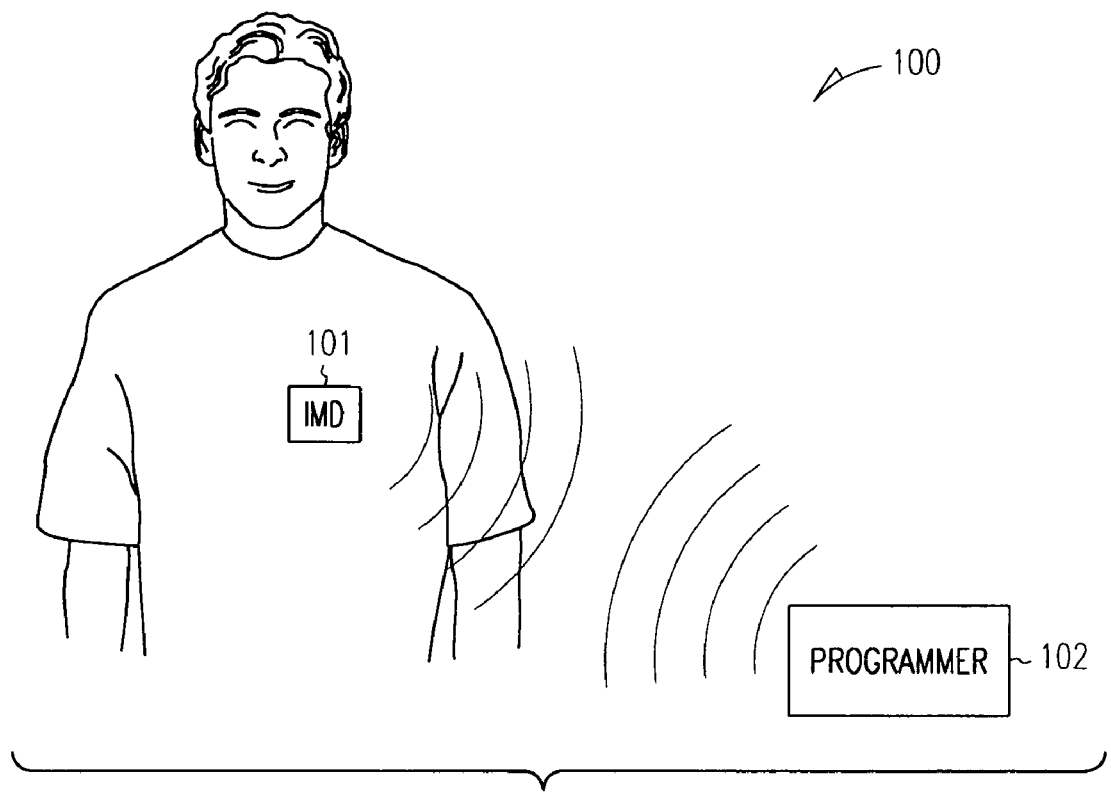
FIG. 1 illustrates a system including an implantable medical device (IMD) and a programmer, according to various embodiments of the present subject matter.

FIG. 1 illustrates a system 100 including an implantable medical device (IMD) 101 and a programmer 102, according to various embodiments of the present subject matter. Various embodiments of the IMD 101 include neural stimulator functions only, and various embodiments include a combination of NS and CRM functions. The IMD can be designed to deliver other therapies, such as drug therapies, along with the neural stimulation and/or CRM therapies. The IMD and programmer are capable of wirelessly communicating data and instructions. In various embodiments, for example, the programmer and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example.

FIG. 1 illustrates an implantable medical device (IMD). Aspects of the present subject matter can be practiced using external devices. FIG. 1 also illustrates that IMD communicating with a programmer. The IMD can also wirelessly communicate directly with a personal digital assistant or other electronic device such as would be used in an advanced patient management (APM) system, which can organize and perform calculations based on recorded data, and later provide the data to a programmer.

Figure 2:
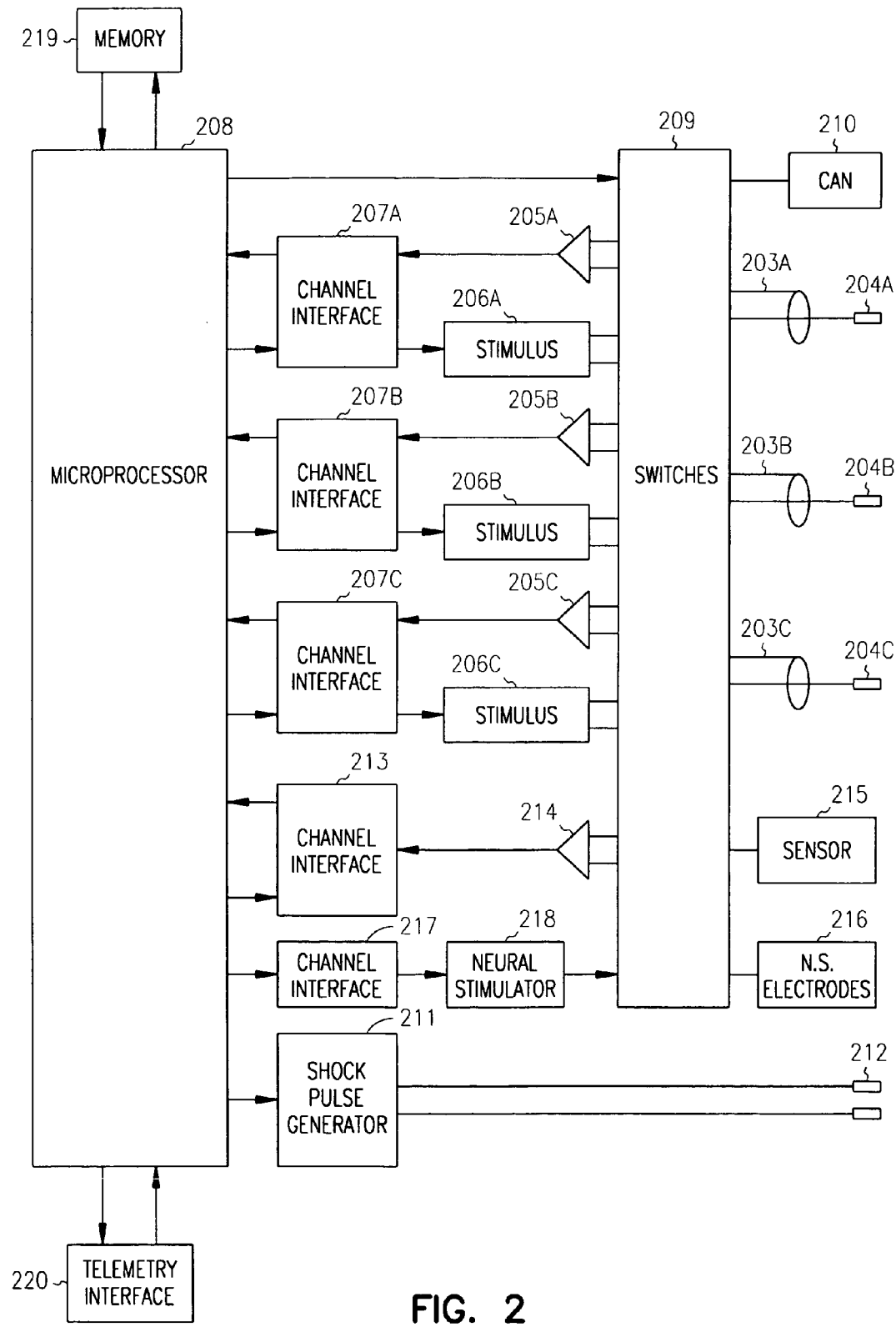
FIG. 2 illustrates a system diagram of an embodiment of an implantable medical device configured for multi-site stimulation and sensing.

FIG. 2 illustrates a system diagram of an embodiment of an implantable medical device configured for multi-site stimulation and sensing. This diagram provides another example of an IMD capable of performing a neural stimulation therapy and a number of CRM therapies. Pacing, as used in the discussion of this figure, relates to electrical stimulation. In various embodiments, the stimulation for a given channel includes stimulation to capture myocardia, neural stimulation or both pacing and neural stimulation. Three examples of sensing and pacing channels, such as can be used in CRM therapy, are designated "A" through "C". The illustrated channels comprise bipolar leads with ring electrodes 203A-C and tip electrodes 204A-C, sensing amplifiers 205A-C, pulse generators 206A-C, and channel interfaces 207A-C. Each of these channels thus includes a stimulation channel extending between the pulse generator the electrode and a sensing channel extending between the sense amplifier and the electrode. The channel interfaces 207A-C communicate bidirectionally with microprocessor 208, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry detects a chamber sense, either an atrial sense or ventricular sense, when an electrogram signal (i.e., a voltage sensed by an electrode representing cardiac electrical activity) generated by a particular channel exceeds a specified detection threshold. Algorithms, including a number of adjustable parameters, used in particular stimulation modes employ such senses to trigger or inhibit stimulation, and the intrinsic atrial and/or ventricular rates can be detected by measuring the time intervals between atrial and ventricular senses, respectively.

The switching network 209 is used to switch the electrodes to the input of a sense amplifier in order to detect intrinsic cardiac activity and to the output of a pulse generator in order to deliver stimulation. The switching network also enables the device to sense or stimulate either in a bipolar mode using both the ring and tip electrodes of a lead or in a unipolar mode using only one of the electrodes of the lead with the device housing or can 210 serving as a ground electrode or another electrode on another lead serving as the ground electrode. A shock pulse generator 211 is also interfaced to the controller for delivering a defibrillation shock via a pair of shock electrodes 212 to the atria or ventricles upon detection of a shockable tachyarrhythmia. Channel interface 213 and sense amplifier 214 provide a connection between the microprocessor and the switch to receive a sensed signal from a sensor 215 for use to guide therapy. Channel interface 217 provides a connection between the microprocessor 208 and a neural stimulator 218, which provides neural stimulation to the neural stimulation electrodes 216.

The controller or microprocessor controls the overall operation of the device in accordance with programmed instructions and a number of adjustable parameters stored in memory 219, including controlling the delivery of stimulation (including neural stimulation and CRM pacing, defibrillation and recharge pulses) via the channels, interpreting sense signals received from the sensing channels, and implementing timers for defining escape intervals and sensory refractory periods. The controller is capable of operating the device in a number of programmed stimulation modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited stimulation modes utilize escape intervals to control pacing in accordance with sensed intrinsic activity such that a stimulation pulse is delivered to a heart chamber during a cardiac cycle only after expiration of a defined escape interval during which no intrinsic beat by the chamber is detected. Escape intervals for ventricular stimulation can be restarted by ventricular or atrial events, the latter allowing the pacing to track intrinsic atrial beats. A telemetry interface 220 is also provided which enables the controller to communicate with an external programmer or remote monitor.

Figure 3:
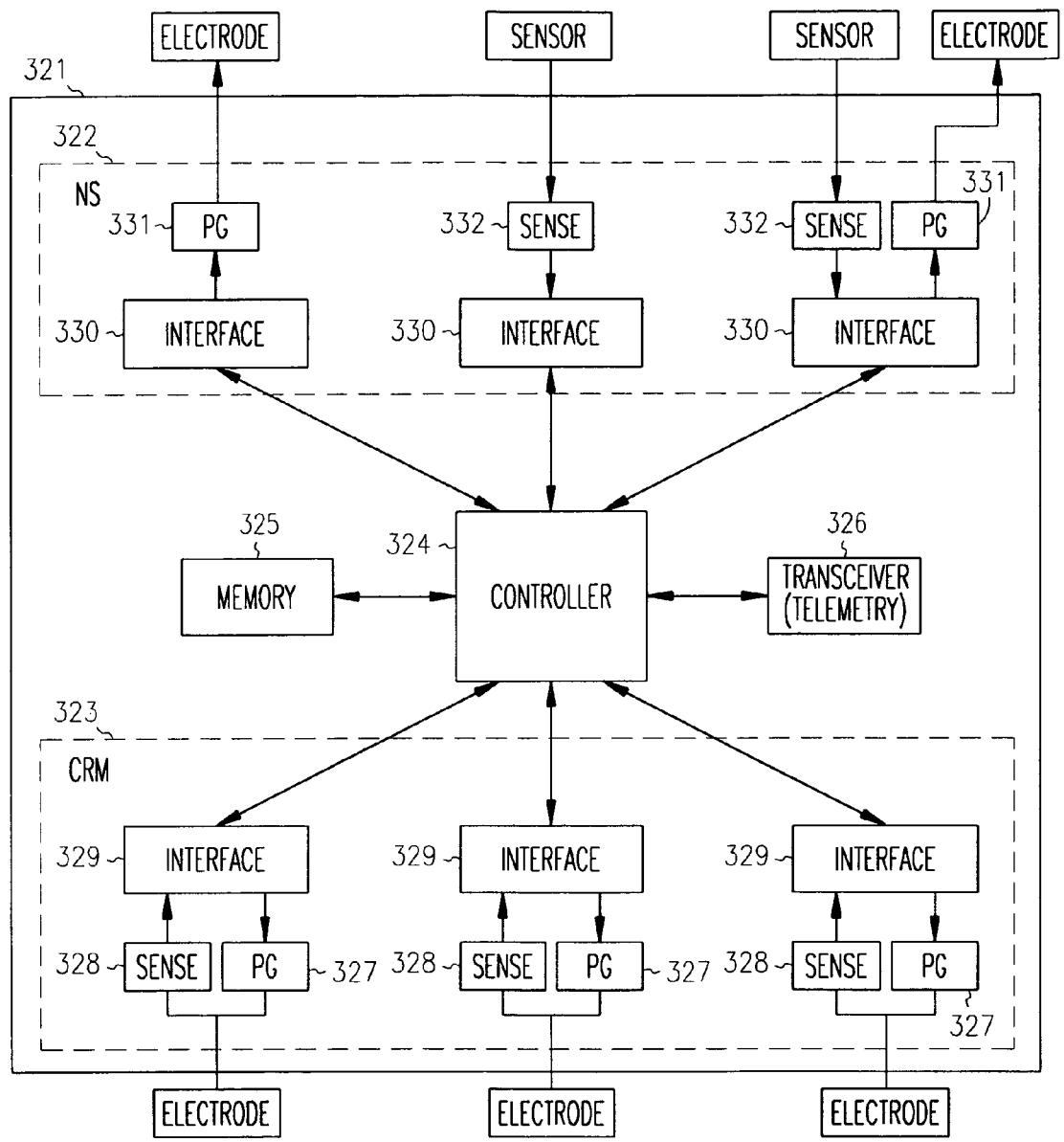
FIG. 3 illustrates an implantable medical device (IMD) having a neural stimulation (NS) component and cardiac rhythm management (CRM) component, according to various embodiments of the present subject matter.

FIG. 3 illustrates an implantable medical device (IMD) 321 such as shown at 101 in FIG. 1 having a neural stimulation (NS) component 322 and cardiac rhythm management (CRM) component 323, according to various embodiments of the present subject matter. The IMD in FIG. 3 provides another illustration in addition to the IMD in FIG. 2. The illustrated device 321 includes a controller 324 and a memory 325. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. The illustrated device 321 further includes a transceiver 326 and associated circuitry for use to communicate with a programmer or another external or internal device. Various embodiments include a telemetry coil.

The CRM therapy section 323 includes components, under the control of the controller, to stimulate a heart and/or sense cardiac signals using one or more electrodes. The CRM therapy section includes a pulse generator 327 for use to provide an electrical signal through an electrode to stimulate a heart, and further includes sense circuitry 328 to detect and process sensed cardiac signals. An interface 329 is generally illustrated for use to communicate between the controller 324 and the pulse generator 327 and sense circuitry 328. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 322 includes components, under the control of the controller, to stimulate a neural stimulation target and/or sense ANS parameters associated with nerve activity or surrogates of ANS parameters such as blood pressure and respiration. Three interfaces 330 are illustrated for use to provide ANS therapy. However, the present subject matter is not limited to a particular number interfaces, or to any particular stimulating or sensing functions. Pulse generators 331 are used to provide electrical pulses to an electrode for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 332 are used to detect and process signals from a sensor, such as a sensor of nerve activity, blood pressure, respiration, and the like. The interfaces 330 are generally illustrated for use to communicate between the controller 324 and the pulse generator 331 and sense circuitry 332. Each interface, for example, may be used to control a separate lead. Various embodiments of the NS therapy section only include a pulse generator to stimulate neural targets such as baroreceptors, nerve trunks, and cardiac fat pads.

According to various embodiments, the lead(s) and the electrode(s) on the leads are physically arranged with respect to the heart in a fashion that enables the electrodes to properly transmit pulses and sense signals from the heart, and with respect to neural targets to stimulate, and in some embodiments sense neural traffic from, the neural targets. Examples of neural targets include both efferent and afferent pathways, such as baroreceptors, nerve trunks and branches such as the vagus nerve and its cardiac branches, and cardiac fat pads, to provide a desired neural stimulation therapy. As there may be a number of leads and a number of electrodes per lead, the configuration can be programmed to use a particular electrode or electrodes.

The leads of the device include one or more leads to provide CRM therapy, such as atrial pacing, right and/or left ventricular pacing, and/or defibrillation. The device also contains at least on neural stimulation lead which is placed in an appropriate location. Some embodiments perform neural stimulation and CRM therapy using the same lead. Examples of neural stimulation leads include: an expandable stimulation lead placed in the pulmonary artery in proximity of a high concentration of baroreceptors; an intravascularly-fed lead placed proximate to a cardiac fat pad to transvascularly stimulate the fat pad; an epicardial lead with an electrode placed in or proximate to the fat pad; a cuff electrode placed around the aortic, carotid, or vagus nerve; and an intravascularly-fed lead placed to transvascularly stimulate the aortic, carotid or vagus nerve. Other lead placements to stimulate other neural targets may be used.

The controller controls delivery of the electrical pulses using a plurality of parameters for at least one programmed electrical therapy of a first electrical therapy type. The controller is adapted to prevent different stimulus, or energy discharges, from occurring simultaneously with a neural stimulation.

Figure 4:
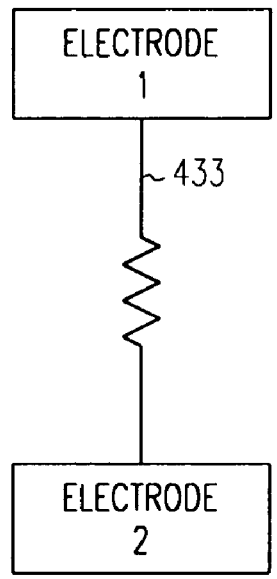
FIG. 4 illustrates a pair of electrodes such as can be used provide an energy discharge, and a desired current path between the electrodes and through tissue.
Figure 5:
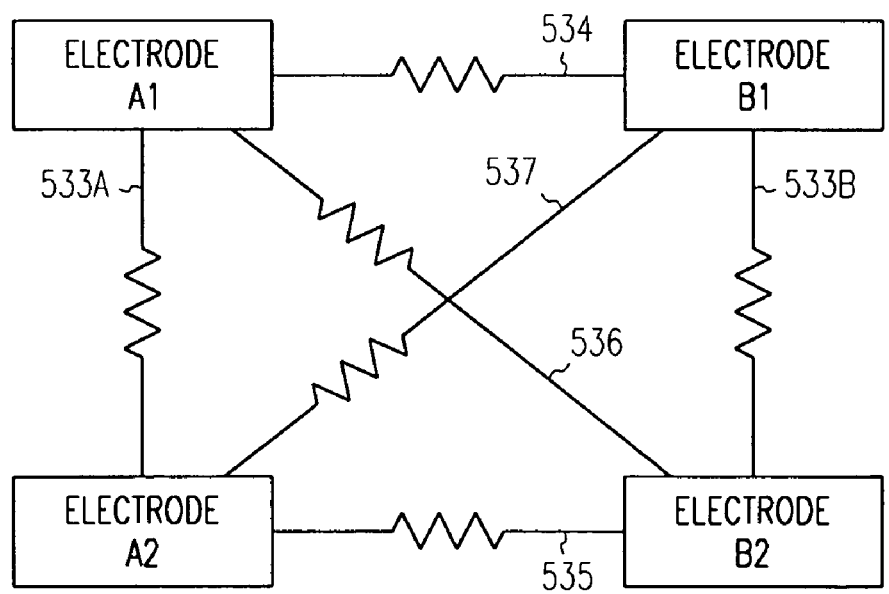
FIG. 5 illustrates a first pair of electrodes for use in providing a first desired energy discharge and a second pair of electrodes for use in providing a second desired energy discharge.

FIG. 4 illustrates a pair of electrodes such as can be used provide an energy discharge, and a desired current path 433 between the electrodes and through tissue. However, there can be problems when more than two electrodes are present. FIG. 5 illustrates a first pair of electrodes A1 and A2 for use in providing a first desired energy discharge via desired current path 533A, and a second pair of electrodes B1 and B2 for use in providing a second desired energy discharge via desired current path 533B. However, other unintended current paths may be presence if there is a potential difference between the electrodes. For example, current flows through current path 534 if there is a potential difference between electrodes A1 and B1, such as may occur if a higher voltage CRM therapy is applied using electrodes A1 and A2 and a lower voltage neural stimulation therapy is applied using electrodes B1 and B2.

Additionally, current flows through current path 535 if there is a potential difference between electrodes A2 and B2, through current path 536 if there is a potential difference between electrodes A1 and B2, if through current path 537 if there is a potential difference between electrodes B1 and A2. Currents in these unintended current paths 534-537 can interfere with the current in the intended current paths 533A and 533B. Depending on the potentials on the electrodes, the unintended current can be summed with the intended current or subtracted from the intended current. The figures illustrate tissue impedance via a simple resistive network. Capacitive and inductive components in the stimulation channels in the lead (s) and IMD can also provide an adverse interaction for the intended current paths.

Figure 6A:
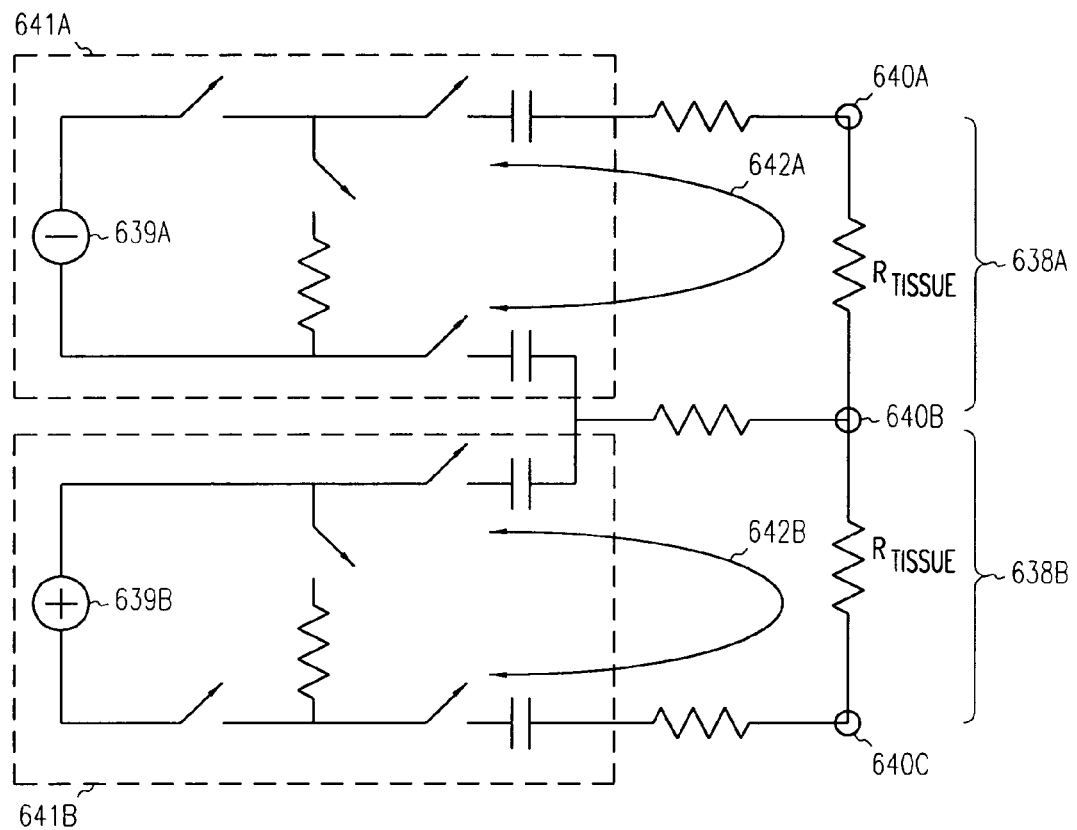
FIGS. 6A and 6B illustrates an electrical schematic of a neural stimulator with two independent pacing circuits and with two energy discharge outputs 638A and 638B, and further illustrates desired current paths and undesired current paths, respectively, for the two energy discharge outputs, and further illustrates intended and unintended current paths.
Figure 6B:
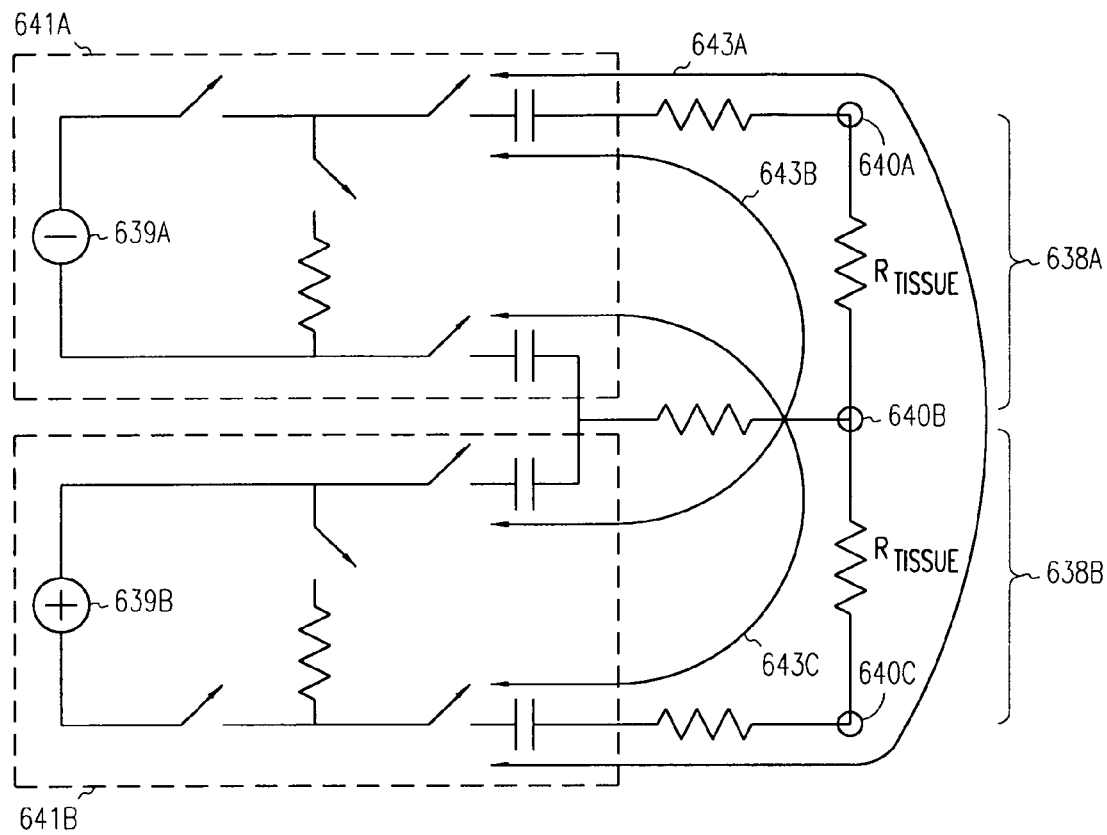

FIGS. 6A and 6B illustrates an electrical schematic of a neural stimulator with two independent pacing circuits and with two energy discharge outputs 638A and 638B, and further illustrates desired current paths and undesired current paths, respectively, for the two energy discharge outputs. The illustrated device includes energy sources 639A and 639B associated with each output. Three electrodes 640A, 640B and 640C are schematically illustrated, along with tissue resistances $R_{Tissue}$ between electrodes 640A and 640B for output 638A and between electrodes 640B and 640C for output 638B. The figure illustrates that energy discharge outputs 638A and 638B associated with the two independent pacing circuits 641A and 641B share electrode 640B. The figure also illustrates a number of switches, capacitors and resistances to model the independent pacing circuits of the neural stimulator.

FIG. 6A illustrates the desired current paths 642A and 642B for each of the independent pacing circuits, and FIG. 6B illustrates the unintended current paths 643A, 643B and 643C between the two independent pacing circuits 641A and 642B. There is a strong interaction among independent pacing circuits due to aberrant current paths between the various pacing sites. The aberrant current paths are present during stimulations (neural stimulation, pacing, recharge cycles, and impedance measurements). The aberrant current paths corrupt the charge balance between the pacing and recharge pulses. This improper charge balance results in a significant capture threshold increase of a site with the lowest independent capture threshold. The increase in the capture threshold is dependent on the pacing impedance, voltage and lead location.

The present subject matter relates to an implantable system that provides neural stimulation at multiple sites, or both neural stimulation and CRM therapy (such as pacing, defibrillation, CRT or a combination). Both these functions could be contained in the same device, or independent implantable devices that communicate through lead-based or leadless means.

For example, some system embodiments include a device that includes port(s), stimulator circuit(s), and a controller to control delivery of both the neural stimulation and the other energy discharge. Some system embodiments include a device that includes port(s), stimulator circuit(s), a first controller to control delivery of the neural stimulation, and a second controller to control delivery of the other energy discharge, where the second controller is adapted to interrupt delivery of the neural stimulation when the other energy discharge is occurring. Some system embodiments include a device that includes port(s), stimulator circuit(s), a first controller to control delivery of the neural stimulation, and a second controller to control delivery of the other energy discharge, where the first controller is adapted to prevent delivery of the neural stimulation when the other energy discharge is occurring. Some system embodiments include a first device to deliver neural stimulation and a second device to deliver another energy discharge and to communicate with the first device, where each of the first and second devices include port(s) to connect lead(s), stimulator circuit(s), and controller (s).

The implantable system prevents the simultaneous release of two or more sources of energy, preventing pulse attenuation or reversal that would otherwise occur. Examples of the sources of energy include cardiac pacing, neural stimulation, recharging, minute ventilation pulses, etc. Various embodiments stagger the application of neural stimulation therapy with the application of other therapies. For example, if a cardiac pacing is required during a prolonged (e.g. 10 second) period of neural stimulation, short windows can be created in the neural stimulation burst during which cardiac pacing could occur. Thus, the present subject matter provides a solution for pulse attenuation or reversal that may result from the simultaneous application of neural stimulation and cardiac pacing.

FIG. 7 illustrates neural stimulation to three neural targets 744A, 744B and 744C, whose stimulation is staggered to prevent simultaneous neural stimulation, according to various embodiments of the present subject matter. In this embodiment, a controller stops a neural stimulation burst (e.g. 744A at 745) before beginning another neural stimulation burst (e.g. 744B at 745). According to this embodiment, the duration of each neural stimulation burst is able to vary, since the controller controls the starting and stopping of each neural stimulation 744A, 744B and 744C.

FIG. 8 illustrates neural stimulation to three neural targets 844A, 844B, 844C, whose stimulation is staggered using predetermined time slots 845A, 845B, 845C, for a predetermined time period 846 within a time domain multiplexing scheme to prevent simultaneous neural stimulation, according to various embodiments of the present subject matter. The time slots can be of equal duration with respect to each other, or some time slots can be longer or shorter than other time slots. If a neural target is to be stimulated, the controller controls the delivery of the neural stimulation to remain in the predetermined time slot for the neural target. In this illustrated embodiment, the controller only needs to apply the different therapies 844A, 844B and 844C in its respective time slot, and does not need to determine when a first therapy is ready to be applied, and interrupt a second therapy to allow the first therapy to be applied.

Figure 9:
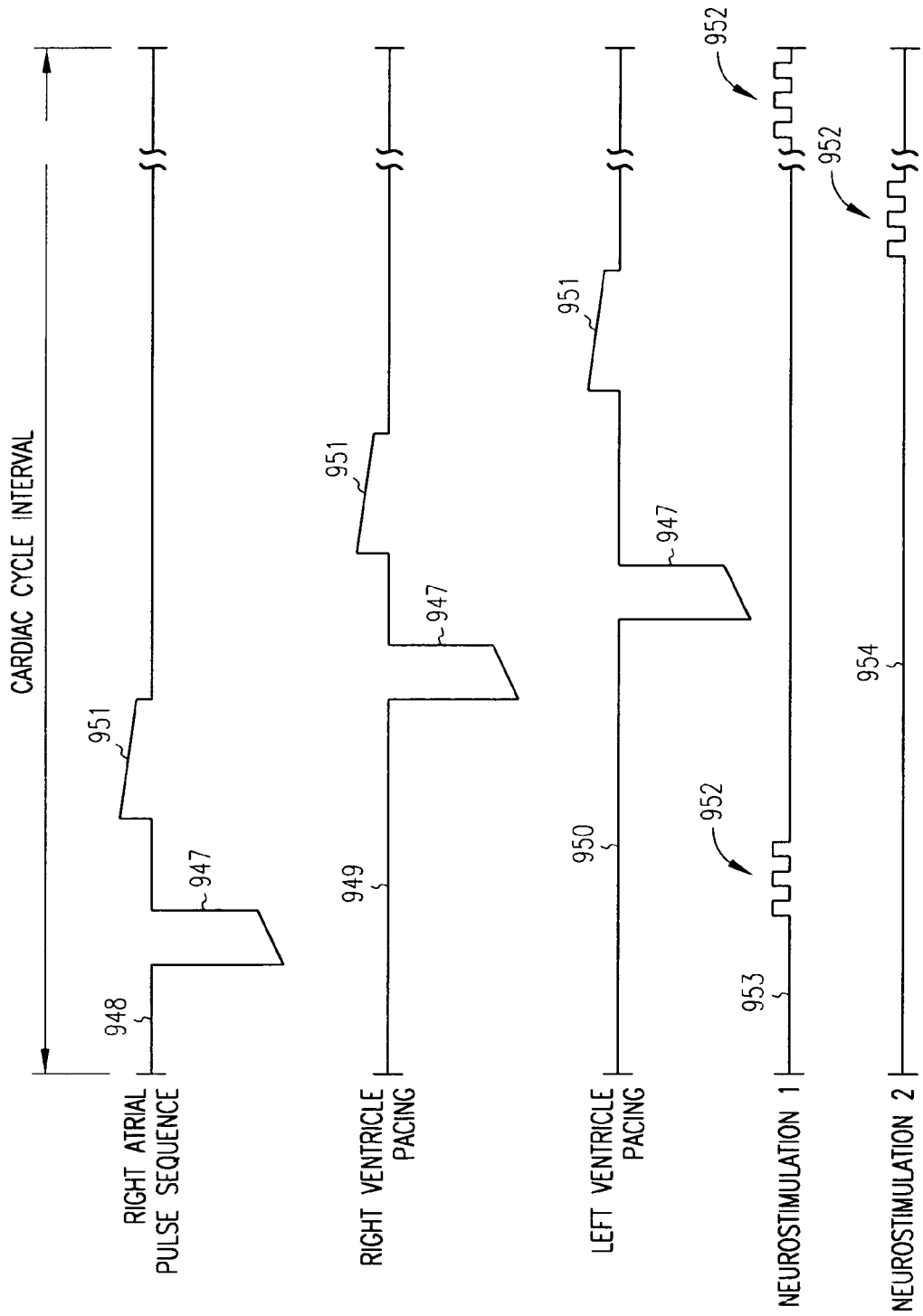
FIG. 9 illustrates CRM pacing and neural stimulation over the course of a cardiac cycle, according to various embodiments of the present subject matter.

FIG. 9 illustrates CRM pacing and neural stimulation over the course of a cardiac cycle, according to various embodiments of the present subject matter. Pacing pulses are represented at 947. The illustrated system paces 947 the right atrium 948, the right ventricle 949, and the left ventricle 950. The figure also illustrates recharge pulses 951 used to reduce an afterpotential resulting from the paces 947.

After a polarizing pulse is applied, an afterpotential of opposite charge is induced in the tissue (e.g. myocardium) at the interface between the tissue and stimulating electrode. After cathodal stimulation, for example, a negatively charged electrode is surrounded by an excess of positively charged ions, and negatively charged ions are repelled. Thus, after a stimulation, the electrode-tissue interface is polarized. The polarization is related to a number of factors, including the amplitude and duration of the pacing stimulus, and the radius, surface area, geometry, surface structure, and chemical composition of the electrode. The afterpotential is temporary and exponentially decays to neutrality. The temporary polarization can be represented as a voltage source at the tissue-electrode interface. Problems associated with afterpotential include sensing problems and capture threshold problems.

For example, afterpotentials can cause an inappropriate inhibition of a pacing pulse unless the sensing circuits are suitably blanked for a time until the afterpotential sufficiently decays. The afterpotential can also change the capture threshold. For example, if a negative potential is applied to the electrode to provide cathodal stimulation in the presence of a positive afterpotential, the negative potential needs to be more negative to compensate for the positive afterpotential and still provide sufficient stimulus to capture the myocardium. The recharge pulse 951 reduces the afterpotential. During the recharge pulse, the electrode polarity is reversed for a period of time following the pulse, which diminishes the polarization at the interface between the electrode and myocardium.

Electrode-tissue interfaces can also be polarized after neural stimulation pulses. A recharge pulse can also be used to reduce the after potential following neural stimulation.

FIG. 9 also illustrates neural stimulation 952 to two neural targets 953 and 954. As illustrated in the figure, only one energy discharge (pace, recharge, neural stimulation) is delivered at a time. That is, the energy discharges are staggered such that one energy discharge completes before another energy discharge begins. The separation between the end of one discharge and the beginning of another discharge can be on the order of about 1 ms to prevent the undesired current paths between electrodes.

Figure 10:
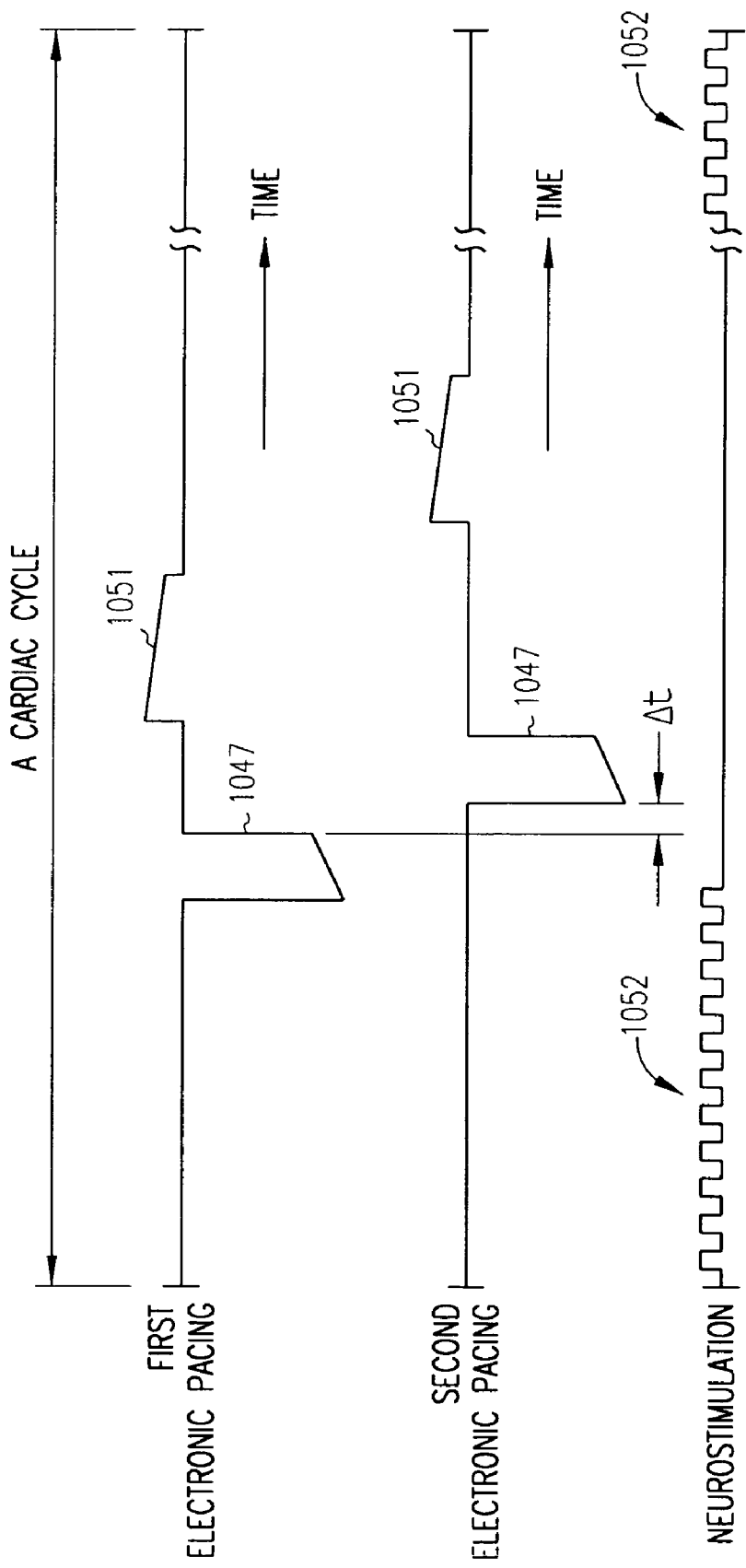
FIG. 10 illustrates CRM pacing and neural stimulation over the course of a cardiac cycle, according to various embodiments of the present subject matter.

FIG. 10 illustrates CRM pacing and neural stimulation over the course of a cardiac cycle, according to various embodiments of the present subject matter. The figure represents three types of energy discharges. They are a pace 1047, recharge 1051 and neural stimulation 1052. Defibrillation pulses and current provided to conduct impedance measurement, such as a transthoracic impedance measurement, are others type of energy discharges. In the illustrated example, the first electrode is paced, then the second electrode is paced, then the first electrode is recharged to remove the afterpotential, and then the second electrode is recharged to remove the afterpotential. The neural stimulation is provided during portions of the cardiac cycle that are not used to provide the CRM pacing and recharge functions.

Figure 11:
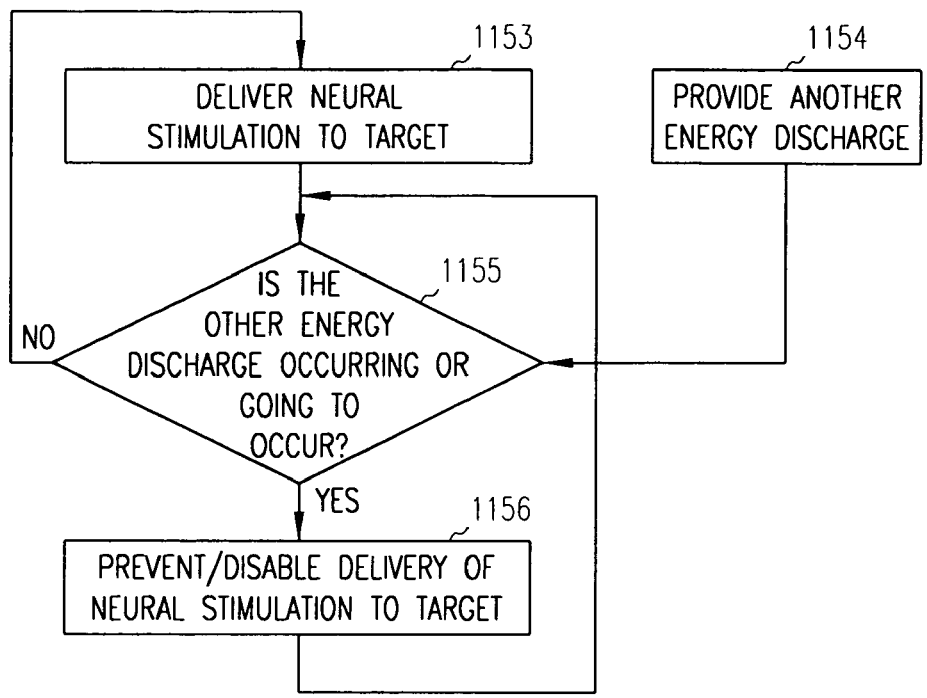
FIG. 11 illustrates a method according to various embodiments of the present subject matter.

FIG. 11 illustrates a method according to various embodiments of the present subject matter. In the illustrated embodiment, neural stimulation is delivered to a neural stimulation target at 1153. There are a number of ways in which neural stimulation can be delivered to a neural target. Some embodiments deliver neural stimulation to a baroreceptor. For example, an expandable lead can be intravascularly placed in a vessel, such as a pulmonary artery, proximate to a baroreceptor. Some embodiments deliver neural stimulation to a cardiac fat pad. For example, the cardiac fat pad can be stimulated using an intravascularly-fed lead to transvascularly stimulate the cardiac fat pad, or can be stimulated using an epicardial lead to place an electrode in or proximate to the cardiac fat pad for use in stimulating the cardiac fat pad. Some embodiments deliver neural stimulation to a nerve trunk, such as an aortic nerve, a carotid nerve or a vagus nerve. For example, the nerve trunk can be stimulated using a nerve cuff placed around the nerve trunk or using an intravascularly-fed lead to transvascularly stimulate the nerve trunk.

Another energy discharge is provided at 1154. Examples of such energy discharges include pacing pulses from a cardiac rhythm management therapy such as a cardiac resynchronization therapy (CRT), a defibrillation shock, a recharge pulse to depolarize an interface between tissue and the electrode, energy discharged to measure impedance such as a minute ventilation pulse, and another neural stimulation to another neural stimulation target. At 1155, it is determined when the other energy discharge is occurring or going to occur. For example, some embodiments receive an interrupt delivered from a CRM module to disable neural stimulation delivery in preparation for an energy discharge from the CRM module. As illustrated at 1156, delivery of the neural stimulation to the neural stimulation target is prevented when the other energy discharge is occurring or going to occur. The process returns from 1156 to 1155 to determine if the other energy discharge is still occurring. If, at 1155, the other energy discharge is not occurring or an indication is not received that it will be occurring, the process proceeds from 1155 to 1153 to continue delivering the neural stimulation to the target in accordance with the neural stimulation therapy.

Figure 12:
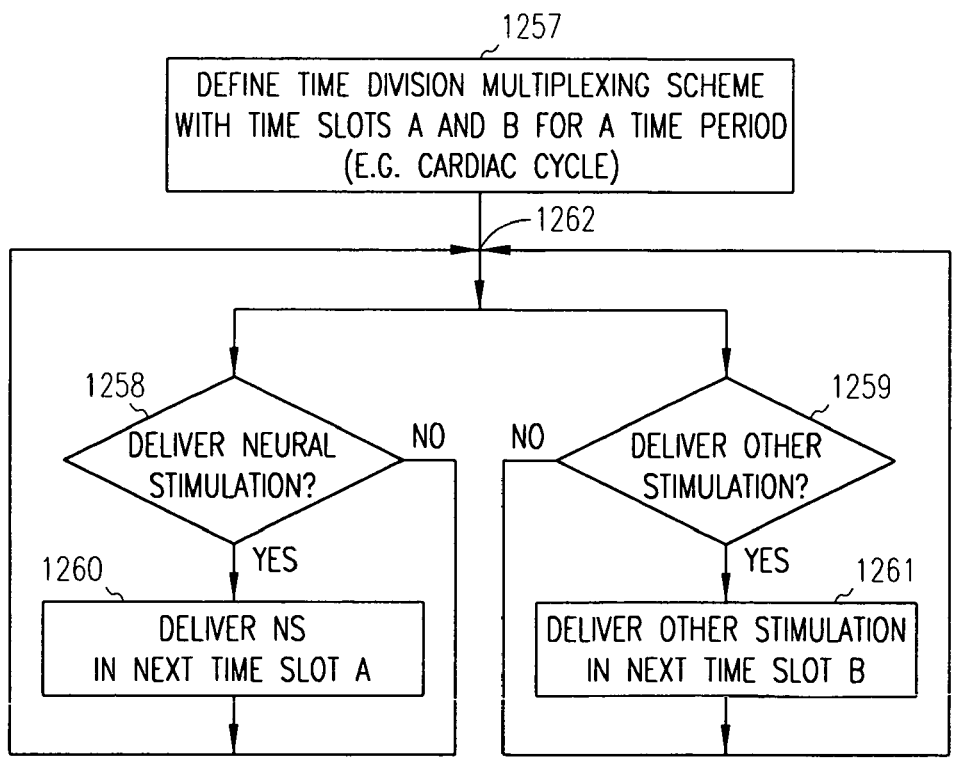
FIG. 12 illustrates a method according to various embodiments of the present subject matter.

FIG. 12 illustrates a method according to various embodiments of the present subject matter. At 1257, a time division multiplexing (TDM) scheme is defined for a time period. The TDM scheme defines at least time slots A and B within the time period. An example of a time period is a cardiac cycle, which provide some benefits for devices that apply both neural stimulation and CRM therapy. Other time periods may be used. For example, a device that provides neural stimulation at multiple neural stimulation targets may use other time periods. It is determined at 1258 whether neural stimulation is to be delivered and it is determined at 1259 whether other stimulation (e.g. pacing, recharging, other neural stimulation, defibrillation, impedance measurement) is to be delivered. If neural stimulation is to be delivered, the process proceeds from 1258 to 1260 where the neural stimulation is delivered in the next time slot A. If neural stimulation is not to be delivered, the process proceeds from 1258 to 1262. If the other stimulation is to be delivered, the process proceeds from 1259 to 1261 where the other stimulation is delivered in the next time slot B. If the other stimulation is not to be delivered, the process proceeds from 1259 to 1262.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An implantable medical system for delivering neural stimulation therapy to a neural stimulation target and for preventing simultaneous delivery of the neural stimulation therapy with another energy discharge, the system comprising:
   at least one stimulator circuit configured to use a first set of outputs to deliver the neural stimulation therapy through a first intended current path to the neural stimulation target, wherein the other energy discharge uses a second set of outputs to provide a second intended current path, wherein the first and second intended current paths are different paths; and
   at least one controller adapted to:
      control the at least one stimulator circuit to stimulate the neural target;
      determine when neural stimulation is to be delivered through the first intended current path;
      determine that, unless overridden, simultaneous delivery of the neural stimulation therapy and the other energy discharge will occur, and override to prevent delivery of the neural stimulation simultaneously with the other energy discharge to prevent an unintended current path between the first and second sets of outputs; and
   an implantable housing configured to be implanted in the patient and to house the at least one stimulator circuit and the at least one controller.

2. The system of claim 1, wherein the at least one controller is adapted to stagger delivery of the neural stimulation with the other energy discharge.

3. The system of claim 1, wherein the at least one controller is adapted to deliver the neural stimulation in predetermined time slots in a time division multiplexing scheme.

4. The system of claim 1, including:
   a first device and a second device adapted to communicate with the first device;
   wherein the first device includes the at least one stimulator circuit, and the at least one controller; and
   wherein the second device is adapted to deliver the other energy discharge.

5. The system of claim 1, further comprising a device, wherein:
   the device includes the at least one stimulator circuit to deliver the neural stimulation, and the at least one controller to control delivery of the neural stimulation;
   the at least one controller includes a controller adapted to control delivery of both the neural stimulation and the other energy discharge.

6. The system of claim 1, further comprising a device, wherein:
   the device includes the at least one stimulator circuit to deliver the neural stimulation, and the at least one controller to control delivery of the neural stimulation;
   the at least one controller includes a first controller to control delivery of the neural stimulation, and a second controller to control delivery of the other energy discharge; and
   the second controller is adapted to interrupt delivery of the neural stimulation when the other energy discharge is occurring.

7. The system of claim 1, further comprising a device, wherein:
   the device includes the at least one stimulator circuit to deliver the neural stimulation, and the at least one controller to control delivery of the neural stimulation;
   the at least one controller includes a first controller to control delivery of the neural stimulation, and a second controller to control delivery of the other energy discharge; and
   the first controller is adapted to prevent delivery of the neural stimulation when the other energy discharge is occurring.

8. The system of claim 1, wherein the other energy discharge includes an energy discharge to capture myocardial tissue from a cardiac rhythm management (CRM) therapy.

9. The system of claim 8, wherein the energy discharge from the CRM therapy includes a pacing pulse.

10. The system of claim 9, wherein, when the pacing pulse is indicated, the controller is adapted to interrupt neural stimulation to provide a window without neural stimulation within which the pacing pulse is applied.

11. The system of claim 8, wherein the energy discharge from the CRM therapy includes a defibrillation shock.

12. The system of claim 8, wherein the energy discharge from the CRM therapy includes a recharge pulse to depolarize an interface between tissue and the electrode.

13. The system of claim 1, wherein the energy discharge includes energy discharged to measure an impedance.

14. The system of claim 13, wherein the energy discharged to measure the impedance includes energy discharged to provide a minute ventilation pulse.

15. The system of claim 1, wherein the energy discharge includes energy discharged by neural stimulation applied to a different neural stimulation target.

16. A system for stimulating a neural stimulation target, comprising:
   means for determining when neural stimulation of the neural stimulation target is indicated;
   means for determining when another energy discharge is indicated;
   means for delivering neural stimulation through a first intended current path to the neural stimulation target when indicated;
   means for providing the other energy discharge through a second intended current path when indicated;
   means for determining that, unless overridden, simultaneous delivery of the neural stimulation and the other energy discharge will occur and overriding to avoid an unintended current path by preventing delivery of the neural stimulation to the neural stimulation target when the other energy discharge is occurring.

17. The system of claim 16, comprising means for staggering delivery of the neural stimulation and the other energy discharge.

18. The system of claim 16, comprising means for delivering neural stimulation in a first predetermined time slot and providing the other energy discharge during a second predetermined time slot in a time division multiplexing scheme.

19. The system of claim 16, comprising means for receiving an interrupt to disable neural stimulation delivery in preparation for the other energy discharge.

20. The system of claim 16, wherein the other energy discharge includes a pacing pulse from a cardiac rhythm management therapy.

21. The system of claim 16, wherein the other energy discharge includes a defibrillation shock.

22. The system of claim 16, wherein the other energy discharge includes a recharge pulse to depolarize an interface between tissue and the electrode.

23. The system of claim 16, wherein the other energy discharge includes energy discharged to measure impedance.

24. The system of claim 16, wherein the other energy discharge includes another neural stimulation to another neural stimulation target.

25. A method for stimulating a neural stimulation target, comprising:
   determining when neural stimulation of the neural stimulation target is indicated;
   determining when another energy discharge is indicated;
   delivering neural stimulation through a first intended current path to neural stimulation target when indicated;
   providing the other energy discharge through a second intended current path when indicated;
   determining that, unless overridden, simultaneous delivery of the neural stimulation and the other energy discharge will occur and overriding to avoid an unintended current path by preventing delivery of the neural stimulation to the neural stimulation target when the other energy discharge is occurring.

26. The method of claim 25, wherein overriding includes staggering delivery of the neural stimulation and the other energy discharge.

27. The method of claim 25, wherein overriding includes delivering neural stimulation in a first predetermined time slot and providing the other energy discharge during a second predetermined time slot in a time division multiplexing scheme.

28. The method of claim 25, wherein overriding includes receiving an interrupt to disable neural stimulation delivery in preparation for the other energy discharge.

29. The method of claim 25, wherein the other energy discharge includes a pacing pulse from a cardiac rhythm management therapy.

30. The method of claim 25, wherein the other energy discharge includes a defibrillation shock.

31. The method of claim 25, wherein the other energy discharge includes a recharge pulse to depolarize an interface between tissue and the electrode.

32. The method of claim 25, wherein the other energy discharge includes energy discharged to measure impedance.

33. The method of claim 25, wherein the other energy discharge includes another neural stimulation to another neural stimulation target.

34. The method of claim 25, wherein delivering neural stimulation to a neural stimulation target includes delivering neural stimulation to a baroreceptor.

35. The method of claim 34, wherein delivering neural stimulation to a baroreceptor includes intravascularly placing an expandable lead in a vessel proximate to a baroreceptor.

36. The method of claim 35, wherein intravascularly placing an expandable lead in a vessel proximate to a baroreceptor includes intravascularly placing the expandable lead in a pulmonary artery.

37. The method of claim 25, wherein delivering neural stimulation to a neural stimulation target includes stimulating a cardiac fat pad.

38. The method of claim 37, wherein stimulating a cardiac fat pad includes using an intravascularly-fed lead to transvascularly stimulate the cardiac fat pad.

39. The method of claim 37, wherein stimulating a cardiac fat pad includes using an epicardial lead to place an electrode in or proximate to the cardiac fat pad for use in stimulating the cardiac fat pad.

40. The method of claim 25, wherein delivering neural stimulation to a neural stimulation target includes stimulating a nerve trunk.

41. The method of claim 40, wherein the nerve trunk includes an aortic nerve, a carotid nerve or a vagus nerve.

42. The method of claim 40, wherein stimulating the nerve trunk includes using a nerve cuff to stimulate the nerve trunk.

43. The method of claim 40, wherein stimulating the nerve trunk includes using an intravascularly-fed lead to transvascularly stimulate the nerve trunk.

* * * * *